United States Patent [19]

Aylsworth

[11] Patent Number: 5,313,820
[45] Date of Patent: May 24, 1994

[54] ULTRASONIC GAS MEASURING DEVICE

[75] Inventor: Alonzo C. Aylsworth, St. Peters, Mo.

[73] Assignee: Puritan Bennett Corporation, St. Louis, Mo.

[21] Appl. No.: 24,785

[22] Filed: Mar. 1, 1993

Related U.S. Application Data

[60] Continuation of Ser. No. 781,819, Oct. 23, 1991, abandoned, which is a division of Ser. No. 444,048, Nov. 30, 1989, Pat. No. 5,060,514.

[51] Int. Cl.$^5$ ............................................. G01N 31/00
[52] U.S. Cl. .................................. 73/24.01; 73/24.06; 73/597
[58] Field of Search ...................... 73/597, 602, 24.01, 73/24.02, 24.03, 24.06, 32 A

[56] References Cited

U.S. PATENT DOCUMENTS

| | | | |
|---|---|---|---|
| 2,568,277 | 9/1951 | Eltgroth | 73/24.01 |
| 3,805,590 | 4/1974 | Ringwall et al. | 73/24.01 |
| 3,981,176 | 9/1976 | Jacobs | 73/24.01 |
| 4,520,654 | 6/1985 | Terhune | 73/24.01 |
| 4,555,932 | 12/1985 | Crosby, Jr. | 73/24.01 |
| 5,060,506 | 10/1991 | Douglas | 73/24.01 |
| 5,060,514 | 10/1991 | Aylsworth | 73/24.01 |

FOREIGN PATENT DOCUMENTS 1112270 4/1983 U.S.S.R. .
2087559 5/1982 United Kingdom .

OTHER PUBLICATIONS

Design Ideas, Detector Measures Acoustic-wave Speed, p. 232, EDN Jan. 8, 1987.
Douglas Scientific Products, Inc., Jan. 1984, Oxyalerts.
Projects Unlimited, 1985, AN-8, Application Note (3 Pages), Selection and Use of Ultrasonic Transducers (month of publication unknown).

Primary Examiner—Louis Arana
Attorney, Agent, or Firm—Paul M. Denk

[57] ABSTRACT

An ultrasonic gas measuring device including a housing, end walls for the housing, the end walls having a gas inlet and a gas outlet provided therethrough, ultrasonic detecting means provided within the housing means, the ultrasonic means having a transmitter, operatively mounted on one end wall, and a receiver, operatively mounted on the other end wall, arranged at spaced locations within the housing, the housing incorporating gas processing means for dividing the gas flow at least at some instance during its flow through the housing, electronic circuitry functioning to detect and generate a signal in cooperation with the ultrasonic detecting means representative of the concentration of gas passing through the housing, the electronic means also generating a reference signal corresponding to the electronic signal delivered to the ultrasonic means, a phase shift provided within the electronic circuitry and effecting a shift of one of said signals to furnish an aligned phased relationship between the two signals whereby the concentration of the gas passing through the housing as detected by the ultrasonic means can be electronically computed and precisely determined by the said electronic means.

10 Claims, 6 Drawing Sheets

ULTRASONIC GAS MEASURING DEVICE

CROSS REFERENCE TO RELATED APPLICATION

This application is designated as a continuation of the application of the same inventor, having Ser. No. 07/781,819, filed on Oct. 23, 1991, now abandoned, both of which applications are owned by a common assignee, which is a divisional application of the application of the same inventor filed in the United States Patent Office on Nov. 30, 1989, under Ser. No. 07/444,048, now U.S. Pat. No. 5,060,514.

BACKGROUND OF THE INVENTION

This invention relates generally to an ultrasonic gas measuring device, for detecting and determining the concentration of a gas being measured, and incorporates means for providing a more effective and efficient determination of the concentration of any gas being detected whether said gas is in the process of being manufactured, or utilized, such as in medical, industrial, or other applications.

Various gas measuring means for determining the concentration of a gas within a particular specimen, such as the concentration of oxygen as used in medical applications, have been available in the art. For example, a Douglas Scientific Products, Inc. has been marketing an oxygen concentrator monitoring device, identified as the "Oxyalert," and which feeds a sample of the oxygen being measured into one area of a transducer assembly, and its sample chamber, and then at a remote location has an exit point for the measured gas, after passing it through an ultrasonic detector that senses the gas composition, and the concentration of specific gaseous components, within its device.

Hudson Oxygen Therapy Sales Co. markets an oxygen concentrator monitoring and regulation assembly, as shown in its U.S. Pat. No. 4,516,424, wherein the concentration of oxygen is detected by passing a gas over a fuel cell terminal that analyzes the gas being measured, by generating a signal as a result of exposure of the gas to the cell terminal, as a means for providing a determination of the concentration of the gas exposed thereto. Other patents to Hudson pertaining to the same technology are shown in the U.S. Pat. Nos. 4,627,860, 4,516,424, 4,561,287, and 4,648,888.

The U.S. Pat. No. 2,984,097 to Kniazuk, et al, discloses a gas measuring apparatus, in which embodiment the development was used to determine the consumption of oxygen being made by a test specimen, and then measuring that degree of oxygen consumed by passing it through what is identified as a sonic generator.

The U.S. Pat. No. 4,616,501 to Mechlenburg, discloses a system that provides an indication of the concentration of at least one gas within a chamber, wherein a pair of operating frequencies generated from mechanical radiant energy are detected, their amplitudes measured, and then compared to a modeled amplitude response representative of a plurality of that gas's concentration to determine the specific concentration of the sample being tested.

The U.S. Pat. No. 4,662,212 to Noguchi, et al, defines a measuring instrument for concentration of gas, that does utilize and ultrasonic vibrator, but wherein the ultrasonic sensor is made humidity proof by utilizing various sealing materials on its outer surface by depositing a film formation by vacuum evaporation through the usage of select elements or compounds for achieving its structure. The device, though, is used for measuring the concentration of a gas passing through the instrument.

The U.K. published patent application No. GB2,087,559A, to Baird, et al, discloses a means for determining gas compositions accoustically, such as by an ultrasonic isolator, for determining and detecting the measurements of a fluid, which presumably includes gases, as well as liquids.

The patent No. SU112270A, of the Soviet Union, discloses a two/phase substance gas concentration acoustic measuring unit, for use for testing a substance, including a gaseous concentration. Phase-sensitive characteristics of the unit are determined during the change of the gas concentration, with the device being utilized upon a pipeline for measuring the gaseous substance and the concentration of that gas.

The U.S. Pat. No. 3,805,590 to Ringwall, et al, discloses an oxygen partial pressure sensor, which utilizes the detection of pressure for determining the amount of oxygen in a helium-oxygen gaseous mixture, and does define the usage of acoustic signal phase shifting to generate electrical signals by which the apparatus maintains oxygen partial pressure within required limits in its delivery of the gas apparently for breathing purposes at various water depths.

Other United States patents relating to detection of gas quantities include the U.S. Pat. No. 4,462,246 to Advani, et al; the U.S. Pat. No. 4,520,654 to Terhune; and, the U.S. Pat. No. 4,581,942 to Ogura, et al, relating to a measuring conduit for flow rate and concentration of fluid.

In addition to the foregoing, a company by the name of Ceramatec, Inc., of Salt Lake City, Utah, has a galvanic oxygen sensor device, which utilizes the fuel cell means for detection in determining the percentage of oxygen within a gaseous mixture.

The current invention, as distinct from the apparatuses and developments described in the prior art devices, provides for a more precise analysis of the concentration of a gas or gases within a gaseous mixture, primarily through the regulation of the gas to be measured as it passes into and through the sensing means, such as by achieving its laminar or divided flow, and through the incorporation of temperature, humidity, and pressure compensation means, furnishes a far more consistent and accurate analysis of the specific concentration of any one of the gases being detected, particularly oxygen, than can be achieved through the usage of the individual or combined prior art teachings.

SUMMARY OF THE INVENTION

This invention contemplates the measuring of gaseous components with far greater accuracy, and incorporates unique methods, and apparatus constructed having components provided therein, for analyzing of gases and gaseous mixtures with increased accuracies through incorporating of electronic circuitry that facilitates the ability to operate and calibrate the device without any need for mechanical adjustment of its ultrasonic sensor.

The use of oxygen concentrators has become common place in the care of respiratory patients, especially in the home care environment. Concentrators provide a breathable gaseous mixture consisting of between about 85% to 95.6% oxygen, an amount of nitrogen and argon, and some other trace gases. As determined by medical testing laboratories, studies indicate that oxygen levels above 85% are effective for therapeutic purposes. Obviously, while the review made herein may analyze the usage of this current invention, and any of the related prior art devices, from the standpoint of medical applications, and more specifically for use with oxygen, it is just as obvious that the gas measuring device of this current invention can be used for any gas concentration detecting purpose, whether it be for the medical industry, or for industry in general.

There have been instances where concentrators have experienced failures that have gone undetected, particularly in the medical industry, where oxygen concentrators are utilized for developing, in situ, a supply of oxygen for use by the patient or patients. As a result, instances have occurred where a patient believing that he/she has been receiving a prescribed level of oxygen, when in fact they were breathing levels well below those that are acceptable. Such predicaments generally have occurred where there was no means or indication of the purity of the oxygen being processed, or which indicators as made available to the patient were inferior or inaccurate, so that any determination made and observed were improper in analysis of the gas being processed. Usually, the home care dealer makes a visit to the patient's home every four to six weeks, which is just a far to risky method for maintaining consistency in review of the operations of an oxygen concentrator, and as a result, there is a significant need for a gas measuring device that can be used readily in combination with the concentration device, easily available to the patient, or the medical practitioner present, to provide a ready indication as to the concentration of the desired gas being made, and processed, at any given moment. Normally, it is the responsibility of the dealer to check the performance of the concentrator in use, and to check the purity of the oxygen being generated by it. Hence, since heretofore checking was done on a multi-week span basis, this makes it quite possible for a failure to exist for a good number of weeks without patient notification or detection. Such occurrences can not only be harmful, but disastrous under certain circumstances.

The oxygen measuring device of this invention provides a means for continuously monitoring of oxygen purity and an immediate notification of any potential failure, or that maintenance must be directed towards any particular item or component, to bring it back up to proper operating conditions. Furthermore, in order to prevent any patient from breathing a gaseous mixture that is far below the prescribed level, and in order to prevent any unnecessary damage to the oxygen concentrator, due to a low oxygen concentration being generated, a detector that can shut down the system upon its activation, as upon reaching a threshold level, and provide an indication that a problem exists, is quite necessary. In the above situations, the patient can switch over to an emergency bottle of oxygen, and telephone the home care dealer for immediate service and/or repair, if means is present to provide a ready reading of the quantity of the gas, such as oxygen, that is being generated, or not properly being created. On the other hand, other applications readily exist for a gas measuring device, one which operates quite effectively and efficiently, also to a high degree or percentage of accuracy, and where particularly it is equally important to know the makeup of any gas or gaseous mixture, and to alert the user of a particular situation and/or to maintain control of a particular situation under conditions where the user can be assured that a specific gas or component thereof is being properly generated.

The gas meauring device of this invention makes usage of the well known principle that different gases have different characteristics in their abilities to propagate, or convey sound waves through them, or to transmit ultrasonic sound waves therethrough. One of the system components of this current invention is the arrangement of a gas sample chamber, or housing, that can sample gases in a continuous flow or in a no-flow or static situation. In this development, a sound wave is transmitted from one end of the gas housing means, or chamber, to its other end thereof. The time that it takes for the foregoing external factors to be detected, compensated for, and with the resultant processed output being once again reprocessed back into electronic signals, such determined parameters are useful for a derivation of analytical information through the application of electronic circuitry, and which information may provide efficient and highly effective and informative data as derived from the measuring device of this invention.

As is well known in the trade, all gases, whether of an individual element, or compounds, have relative properties that have been previously calculated and determined. The following chart discloses such information with respect to those type of gases that may be readily applied and utilized for both medical and industrial applications.

| Substance | Formula | Density (gm/L) | Velocity of sound (m/s) | Change V/ Change T (m/s degree C.) |
|---|---|---|---|---|
| Gases (0 degrees C.) | | | | |
| Air, Dry | | 1.293 | 331.45 | 0.59 |
| Argon | A | 1.783 | 319 | 0.56 |
| Carbon dioxide | $CO_2$ | 1.977 | 259 | 0.4 |
| Carbon monoxide | CO | 1.25 | 338 | 0.6 |
| Helium | He | 0.178 | 965 | 0.8 |
| Nitrogen | $N_2$ | 1.251 | 334 | 0.6 |
| Nitrous oxide | $N_2O$ | 1.977 | 263 | 0.5 |
| Oxygen | $O_2$ | 1.429 | 316 | 0.56 |

The gas sensor assembly of this current invention contains those items and components necessary to effect a transmission and reception of ultrasonic waves, that cooperate in conjunction with electronic circuitry which is responsive not only to a detection of the speed of transmission of such waves, through a gas specimen, but likewise takes into consideration and compensation for, after computing from sensors data relative to temperature, pressure, and humidity conditions, to alleviate their effects, and utilizes such determined data to process, electronically, the circuitry information and signals derived, with respect to precise wave transmission, to provide a more accurate output of information relative to a select gas. From that information, as derived, when compared with known conditions for transfer of ultrasonic waves through a gas of select concentrations, which may be determined from 0% to 100% capacities, the device of this invention can readily determine and provide an immediate and accurate output of the concentration of a particular gas passing through this sensor assembly, and which provides an immediate readout, as for example, of the amount of generation of such gas, such as oxygen, from an operating concentrator.

The gas sensor assembly or measuring device of this invention incorporates a gas inlet, which is designed to accept supply tubing, as from a concentrator, so as to provide a direct admission of a gaseous sample, to be detected and measured, for entrance into the housing means of this assembly. The gas inlet allows for the flow of the gas initially into an inlet chamber or compartment of the housing means, with the inlet chamber thereby allowing the gas to flow over a temperature sensor and provides an immediate response to any changes in temperature that may occur within the gas product as represented through its gas sample The gas then enters into the sample chamber of the housing means, and in this particular invention, the gas is processed to provide for its divided or laminar flow into the chamber, for reasons as will be subsequently described and analyzed The housing means of this invention incorporates a pair of end walls, and which end walls include access apertures through them, with these access apertures providing for a conversion of the gaseous flow stream into that more laminar or divided flow, as the gas passes through a series of such apertures provided within that end wall through which the gas sample is allowed access into the housing means. Because of the design of the sample gas chamber which allows for the flow of the sample or specimen gas through its series of apertures, a smooth laminar flow of the gas, at significantly reduced turbulence, is accomplished as the gas passes into the device, at the inlet end of the housing, and thereby allows for the gas to flow under such conditions at least initially through the housing means, or its chamber, and to the receiver end, or outlet end wall of the housing means. At such location, the outlet end likewise includes a series of apertures, that provides for an exiting of the gas sample from the device, again under conditions that induce a laminar or divided flow of gas from the measuring device of this invention. Smooth laminar or divided flow of gas through the housing means of this assembly has been found quite necessary for the purpose of attaining more accurate measurements and the detection of the specific gas component in the sample chamber, for a variety of purposes. Initially, divided or laminar flow of the gas as it passes through the measuring device of this assembly substantially reduces if not diminishes any turbulence in the flow of the gas sample as it passes through the housing. Without such reduction in turbulence, and has been found through usage of some of the prior art type of gas analysis devices as previously explained in the background of this invention, propogation delays in the passage of ultrasonic or other detection means through a chamber can be encountered, causing aberrations in data, and which tend to provide substantial distortions in the readout of the information received from the sampling device, which, as can be readily understood, induces inaccuracies in the determination of the quantity of the particular gas being measured. Such propagation delays have been found to cause an erratic output type of signal, from the detection means, in addition to a slower response time, which causes inaccuracies for the measurements as detected for the gaseous sample under analysis.

In the current invention, it is desired to provide for the mounting of the sonic detector in a longitudinal dimension along the length of the housing means of this assembly, with the transmitter means of the ultrasonic waves being located in proximity or upon the interior of the inlet end wall, while the receiver element of the ultrasonic means is mounted upon the outlet end wall of the said device. Thus, exposure of the gas sample, passing by means of its laminar or divided flow through and longitudinally of the housing assembly, is detected substantially over the length of the measuring device, in order to provide greater accuracy through analysis of the expanded form of signal that may be derived and detected from the exposure of the ultrasonic waves to the gas under consideration and sampling. Some prior devices have located the ultrasonic detectors at a perpendicular with respect to the gas flow, and it is believed that this type of detection is just too brief of a span for analysis through exposure of the ultrasonic waves to any gas flow being considered, and therefore, may not provide adequate signal that furnishes sufficient information to attain efficient analysis of the gas sample under consideration. In addition, by arranging the ultrasonic means in a position for detecting and sampling longitudinal flow along the length of the gas being sampled, it has been found and considered that a quicker response can be attained from a measuring device of this construction, since a faster exchange of information can be derived through the exposure of the ultrasonic waves over a greater length of the material gas flowing through the housing means, thereby adding to the degree and quantity of gaseous exposure for attaining an output of information relative to this device.

Also embodied within the housing means of this invention, and intermediate the end walls of its assembly, is a sound absorbing material, or a cylinder of such, with the preferred embodiment being fabricated of a layer of felt like filter material having a texture that absorbs unwanted sound waves, so that the gas sample which passes in a divided flow for a brief dimension through the filtering means, before it passes into the interior of the housing, and within its chamber, will have any and all standing waves removed therefrom, with turbulence being minimized, so that greater accuracy in measurements can be obtained. For example, where the gas flow through the sampling device, as can be found in prior art assemblies, do not compensate for or remove turbulent flow of the gas sample through their device, or in which some degree of turbulent flow occurs, such as to cause the disruption in the direct flow of the gas through the sampling means, or in the event that the sounds waves themselves may be deviated from their linear course of travel, such detriments can and have provided irregulaties in the accurate output of information from previous gas samplers. The current invention, on the other hand, is designed structurally to provide for as direct linear flow of gas through the measuring device, and likewise, has internal structure that enhances and assures the direct and longitudinal flow of the ultrasonic waves through the device, so that a clean and clear detection, and generation of information therefrom, can be made, to provide efficiency in the output of computed information, in addition to its consistency. It is believed that this cannot occur with respect to the usage of some prior art devices. This accoustical element, or filter means, is designed not only to reduce standing wave interference quite effectively, but also to help insure and continue the laminar flow of the gas sample throughout the chamber of the housing means of this invention. The flow of gas through the end wall apertures allows the gas to flow directly into this filter means, at which time a quantity of the gas sample is then directed into the ultrasonic chamber, in a nonturbulent manner, for its flow along the length of the housing means, where once again it passes into the filter element and through the exit apertures furnished through the outlet end wall of the device. Likewise, because of the presence of the filter element along the length of the interior wall of the chamber, it has a tendency to prevent, as previously explained, the diversion or redirection of any of the ultrasonic waves, thereby continuing that laminar and direct flow for both the gas sample, and the ultrasonic signal, as the two together pass longitudinally through the housing means of this invention.

After the gas sample passes through the sample chamber of this invention, it then exits the sample chamber by way of its flow through the apertures at the receiver element of the ultrasonic means, which is the preferred operation for this device. Although it is just as likely that the gas flow may pass in a direction opposite to that of the sonic waves, or in a direction against the flow of ultrasonic waves through this measuring device. It is believed that accuracy of results will be attained in either instance. Such will simply require a precalibration of the various parameters of operation of the device, to compensate for any variations that may occur as a result of opposite gas flow in a direction against the passage of the ultrasonic waves through the gas as it passes through this measuring device.

As previously explained, means are provided for furnishing temperature, pressure, and humidity sensing within the chamber, and particular of the gas passing therethrough. This means may include the arrangement of a separate chamber, or chambers, at either the entrance end and/or exit end of the housing means. Temperature sensing may be made in one of such chambers, such as at the entrance end, while pressure and/or humidity compensation may be detected and determined at a chamber provided at the exit end of the housing means. Or, it is possible that all three of these means for sensing may be furnished within one separate chamber of the device. On the other hand, it is just as likely, although not as desirable, to provide for detecting such parameters for the flowing gas directly within the main chamber of the housing means, as through sensors, but it is of concern that such means for detection may cause undersirable turbulence within the flow of the gas sample, which, as previously explained, is sought to be minimized and reduced, or eliminated by means of the addition of the filter element within the chamber of the housing means of this invention.

There are both a gas inlet, and a gas outlet, provided in cooperation with each of the respective end walls of the gas measuring device of this invention. Supply gas tubing may be pressure fitted onto these inlet and outlets, as can be readily understood, when this gas measuring device is installed. Since it is of critical importance that the ultrasonic detection means of this invention be preadjusted so as to provide extreme accuracy in its usage and detection of any gas sample passing through this device, as can be readily understood, it is desirable to provide an adjustment means to the setting of the ultrasonic detector, and this can be arranged as follows. One of the end walls of this current invention may be slidably mounted within the housing means, or more specifically within its inner chamber, and be readily adjusted longitudinally therein, in order to attain a precise and fine setting of the device, in preparation for its usage. In the preferred embodiment, the exit end wall of the device is adjustable, may be slid internally, or shifted outwardly, in order to attain a precise setting in the dimension between the ultrasonic transmitter and receiver. Then, once the ultrasonic means is set, various epoxy, or an adhesive, may be filled into the ends of the housing means, externally of their end walls, so as to provide a precise and permanent set to the measuring device as assembled, and readied for a particular application in measuring of specific gas samples.

Because of mechanical tolerances in the manufacturing process, of the measuring device of this type, it is difficult to maintain a fixed distance from sensor to sensor between the transmitter and receiver elements. Should a number of gas sensor assemblies be manufactured using a fixed mechanical distance, from the transmitter element to the receiver element, then the time span for transfer of ultrasonic waves between these elements under controlled conditions will obviously be different from sensor to sensor. Using sensors that exhibit different time-to-fly characteristics will yield different amounts of gain required to accurately compensate for temperature effects, if not also for remedying and compensating for variations in detected humidity and pressure under given circumstances of usage. Mechanical adjustment to fix the span, between the transmitter element and the receiver element, for each sensor to a predetermined value, for a given temperature, pressure and humidity, is possible because of the ability to shift at least one of the end walls, mounting either a transmitter element or receiver element, for the gas sensor assembly as previously explained. The gas sensor assembly of this invention has provisions, therefore, for adjusting that time for transmission of ultrasonic waves over a select distance to predetermine values, depending upon the type and conditions of the gas sample being measured.

It is, therefore, the principal object of this invention to provide greater accuracy in the usage of ultrasonic means for providing the measurement of gas.

Another object of this invention is to provide means for furnishing smooth laminar or divided flow of a sample gas through an ultrasonic analyzer.

Still another object of this invention is to provide a simple and effective means for reducing standing wave conditions within a gas detection and sampling device.

Yet another object of this invention is to provide a means for attaining compensation for temperature conditions within a gas sample flow without interfering with ultrasonic wave analysis.

Still another object of this invention is to provide means for furnishing pressure and humidity analysis, and compensation as a result thereof, so as to assure quality and highly precise outputs in the measurement of a sample gas passing through an ultrasonic analyzer.

Still an additional object of this invention is to provide electronic means for sensor and output calibration to assure significant efficiency in the analysis of a gas sample passing through this ultrasonic gas measuring device.

These and other objects may become more apparent to those skilled in the art upon reviewing this summary of this invention, and upon undertaking a study of the description of its preferred embodiment, in view of the drawings.

DESCRIPTION OF THE PREFERRED EMBODIMENT

Figure 1:
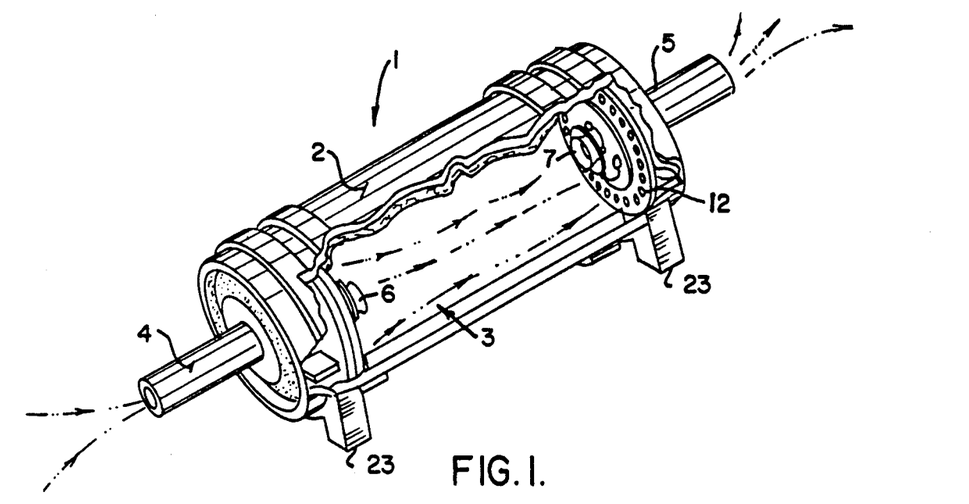
FIG. 1 provides an isometric view, partially cutaway, of the ultrasonic gas measuring device of this invention.

In referring to the drawings, and in particular FIG. 1, the ultrasonic gas measuring device 1 of this invention is quite clearly disclosed. The device includes a housing means 2 which is of rather cylindrical design, although other shapes for the housing means obviously can be made for this development. The cylinder incorporates an inner chamber 3 therein, and it is through this chamber that the various means for detecting, in addition to the gaseous means being detected passes. For example, the flow lines as shown within this chamber depict the passage of the gas sample moving therethrough, while simultaneously, the ultrasonic waves from the ultrasonic transmission means likewise passes along the length of this device. A gas inlet 4 is provided at one end of the housing, while a gas outlet 5 is disclosed at its other end.

Within the chamber 3 of the housing means includes the ultrasonic wave transmitter 6 and the ultrasonic wave receptor or receiver 7.

Figure 2:
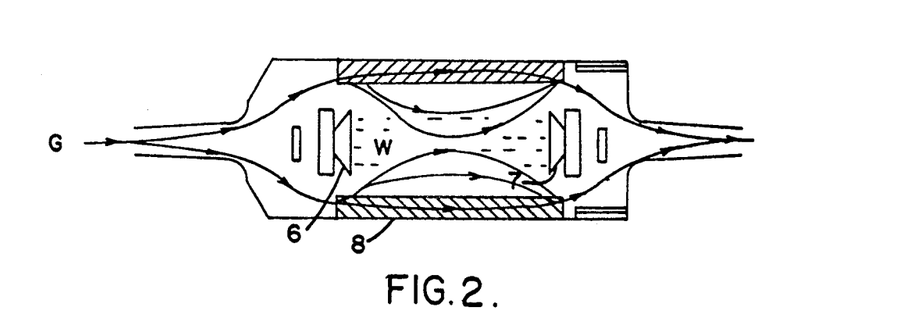
FIG. 2 is a schematic cross-sectional view of the measuring device of this invention disclosing the passage of a gaseous sample therethrough.

In referring to FIG. 2, the schematic for this particular development is accurately shown. It can be seen that the gas sample as at G, passes into the gas inlet 4, and passes through the inlet end of the housing means 1, and is directed into a gas absorber 8, before a substantial portion of it is directed into the chamber 3, where it is directed to flow by means of its divided or laminar flow through the said chamber, and therein be exposed to the ultrasonic waves of transmission emitted from the transmitter 6, as they pass towards the receiver 7. These ultrasonic waves are depicted at W. Thus, it is the divided or laminar-like flow of the gas through the chamber 3, as subjected to the linear flow of the ultrasonic waves W therethrough, which provides for accuracy in detection, precalibration, and measurement of any gas sample passing through this invention.

Figure 3:
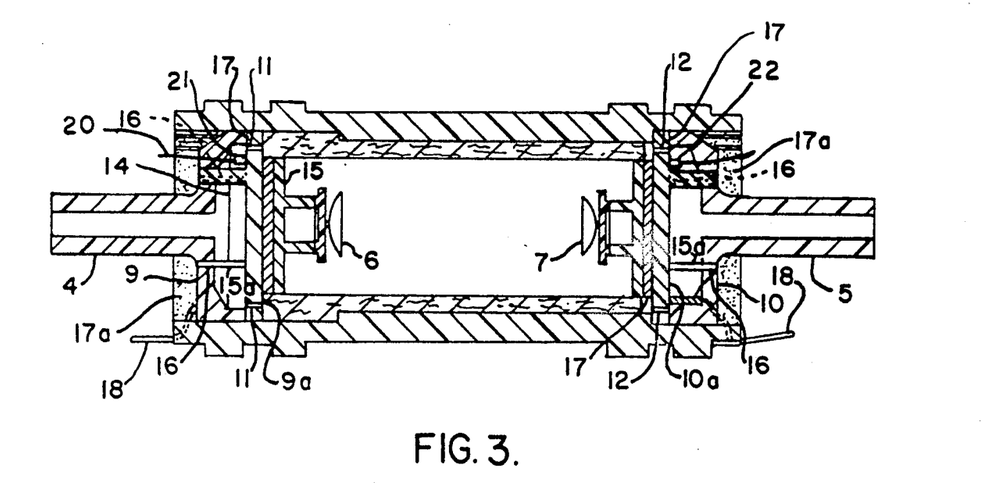
FIG. 3 is a longitudinal sectional view of the gas measuring device of this invention.
Figure 4:
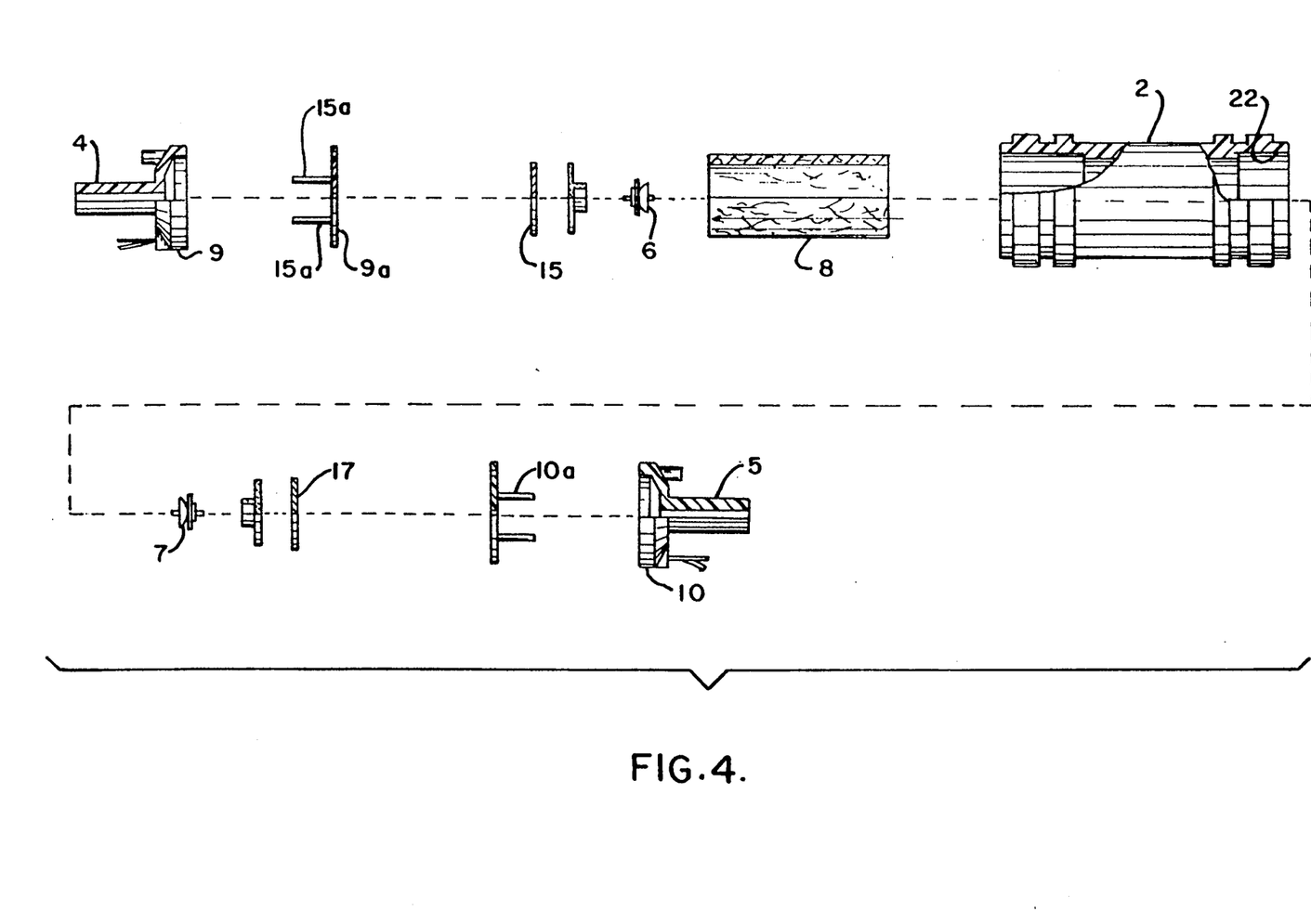
FIG. 4 is an exploded view, in partial section, of the gas measuring device of this invention.

In referring also to FIGS. 3 and 4, the actual physical features or structure of this invention are more accurately disclosed. As can be seen, the cylinder incorporates its gas inlet 4 and gas outlet 5, in the manner as previously explained. But, each of these inlets and outlets are integrally structured, respectively, to form their cavity shaped end walls 9 and 10, respectively. Slide mounted to each end wall, overlying their cavity shape are the apertured disks 9a and 10a, respectively. These provide a path for flow for the gas into the inlet 4, into the cavitied end wall 9, through the apertured disk 9a, for divided flow into the cylinder filter of filter 8, for laminar flow into the chamber 3. The gas exits from related components 10a, 10 and 5, at the outlet end. As can be noted, each of these disks include a series of apertures, as at 11 and 12, therethrough, generally arranged around the circumferential periphery of each, so that as gas G enters into the measuring device, and encounters the inlet end wall 9, the gas is diverted outwardly for passage through these series of apertures 11, for direction into that gas filter and diffuser 8, which has a tendency, as previously explained, to reduce turbulence of the gas as it is then directed and passed into the chamber 3, for movement along its length, and within the influence of the ultrasonic wave pattern W, until such time as the gas is then redirected outwardly of the chamber and back into the filter means 8, for passage through the apertures 12 of the disk at the outlet end wall 10, for discharge through the gas outlet 5, as noted.

The specific structure of each of the end walls 9 and 10 and their related slide disks are more accurately disclosed in FIG. 4. As can be seen, each of the end walls includes either their gas inlet or gas outlet, depending upon their location within the assembled housing means, with the gas conduit integrally connecting with its back wall 9, as noted, with the back wall forming a compartment or cavity therein, as at 14, and into which various detecting means, as will be subsequently described later. The disk 9a has mounted thereon a plate 15 that supports the transmitter 6. Also the disks 9a and 10a incorporate those series of circumferentially arranged apertures, such as the apertures 11 and 12, as aforesaid. The disks each have positioning pins and electrical contacts that slide fit through their respective walls 9 and 10, (See FIG. 4), and are aligned into position by means of the pins 15a that locate within openings 16, so as to guide the plate into position, for resting against the peripheral edges 17 of the cavitied end wall structures, as can be seen. When assembled in this manner, the pins and the end walls supporting them and their disks can be sealed by means of an adhesive, or epoxy, as at 17a, to close off and seal the chamber 3 at each end. But, before this step, the end walls must be inserted and adjusted within the chamber 3 of the housing means 1. Various electrical leads, as at 18, from their ultrasonic sensors, extend through the disks 9a and 10a, and extend through the back walls 9 and 10 of the end wall structures, and are directed for connecting with the electronic circuitry of this invention. In addition, supplemental leads, as at 20, may extend into the compartment 14, and connect with either a temperature dectection and compensation means 21, or with a pressure or humidity sensor 22, and likewise have their leads extend out of the back wall 9, and directed for electrically connecting with the electronic circuitry of this invention for further processing.

As can be seen, the housing means 1, and more specifically its cylinder 2, may include mounts, as at 23, so as to facilitate the device's mounting directly to a printed circuity board, of the type as to be subsequently described, so as to transmit electronic data, or signals, to the circuit board for further processing of the detected gas signal, or for use in compensating for the variations in any temperature, humidity, or pressure, or in the setting of this gas measuring device itself, in preparation for its sustained application and usage.

In the setting of this gas sensor assembly in preparation for its application, it is necessary to provide for its precalibration with respect to the particular type of gas to be detected and measured. Hence, when the gas measuring device is assembled, at least one of these end walls 9 or 10 will slidably fit within its cylinder 2, and will have adjustability lengthwise, within the cylinder, to provide for a very precise setting in the linear distance between the transmitter 6, and the receiver 7, during preparation. Generally, the end wall 9 at the inlet end of the cylinder will have a more fixed disposition when inserted within the cylinder 2, but the outlet end wall 10, as can be seen, slidably fits within the interior and proximate end of the cylinder 2, with the cylinder 2 having a length of internal segment or counterbore, as at 22, that may receive the end wall 10 for its sliding insertion therein, for a distance of approximately 30% of the overall length of the cylinder 2, so that there will be ample room provided for shifting of the said outlet end therein, to provide a wide range of its lengthwise maneuvering to be performed upon it for furnishing very accurate precalibration of the gas sensor during its calibration for eventual application in the detection and measuring of select gas samples. Following this, the epoxy plug 17a will be filled within this end of the cylinder 2 to seal the finely adjusted device in tact.

Figure 5:
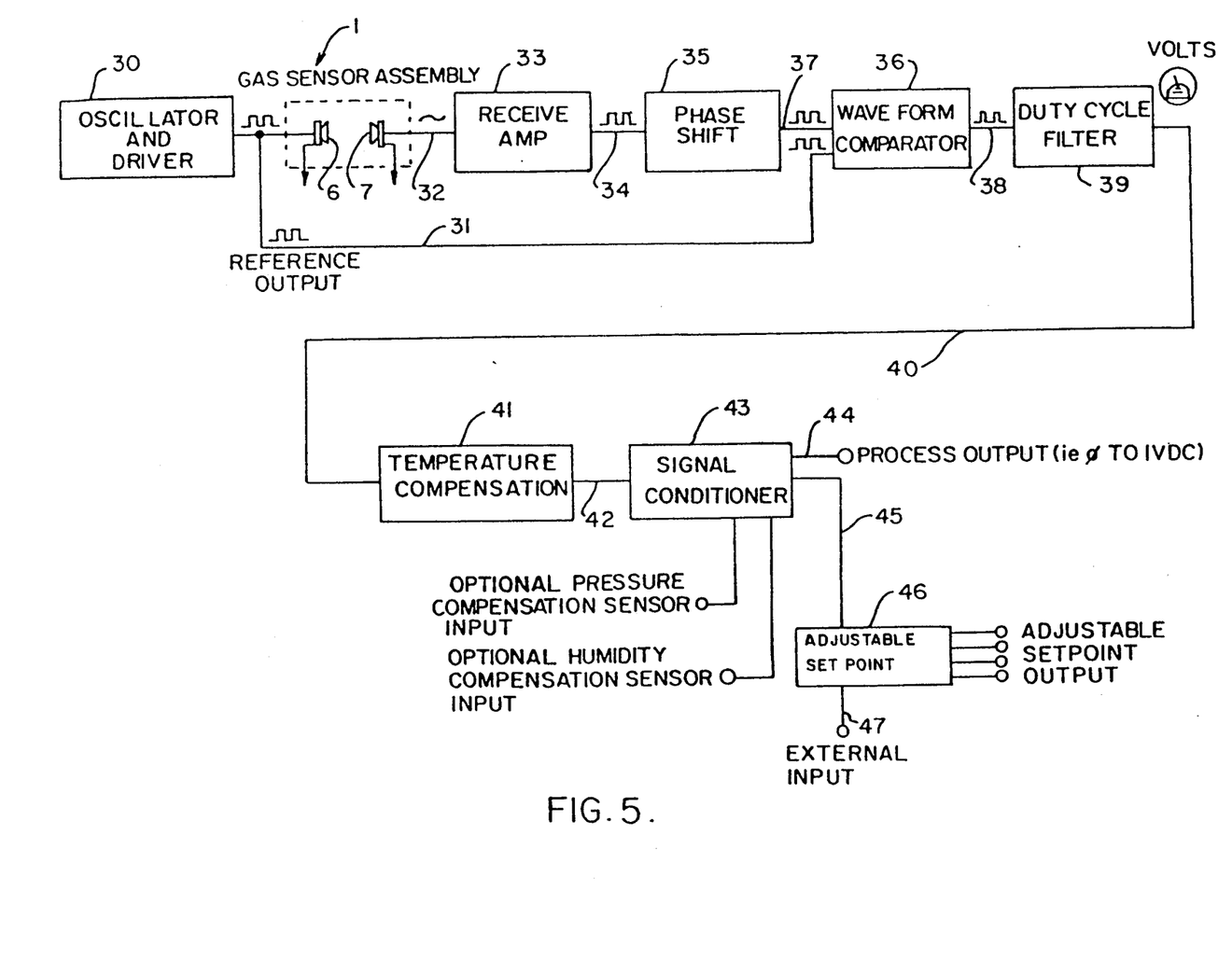
FIG. 5 is a block diagram of the structure and operation of the gas measuring device of this invention.

In referring to FIG. 5 of the drawings, a block diagram of the electrical components utilized in and to furnish operational characteristics for the gas sensor 1 of this invention are readily disclosed. The sensor 1 can be readily seen therein, with its ultrasonic transmitter element 6 and its ultrasonic receiver element 7 being disclosed as interconnecting within the circuitry of this invention. The oscillator and driver circuitry 30 provides an ultrasonic signal that drives the transmitter element within the sample chamber of the gas sensor assembly 1, as previously described. This oscillator and driver component is available from Motorola Company, of Phoenix, Ariz., under part No. MC14049. The oscillator and driver incorporates a crystal resonating device that converts the inputted electrical signal into a clock frequency, which is amplified by integrated circuitry into a square wave pattern that is used to drive the transmitter element 6, which converts the signal into a sonic wave pattern. The ocilator and driver 30 also directs the square wave signal representative of the reference output along the circuit line 31. The ultrasonic receiver element 7 accepts the ultrasonic sound wave from the transmitter and its output as generated is a sign wave conducted along the circuit line 32. This ultrasonic gas sensor assembly 1, and more specifically the transmitter 6 and receiver 7 are available from Murata, Inc., of Smyrna, Ga., as part Nos. MA40A3R - S. The wave signal is transmitted over the circuit line 32 and it then is amplified into a square wave output by a receive amplifier 33, which is an integrated circuit and its associated componentry, available from Motorola Corporation, under part No. CM 393. Its output is conducted along circuit line 34 in the square wave signal configuration, as noted, and is transmitted to the input of a phase shift circuitry 35 where the received signal is positioned or phase shifted and inputted into the wave form comparator 36. The phase shift 35 is fabricated of three integrated circuitries, which are available from Motorola Corporation, under Model Nos. MC 14093 and MC 14584, and from Maximum Integrated Products, Inc., of Sunnyvale, Calif., under Model No. ICM 7556. The wave form comparator receives the reference output signal transmitted by way of the circuit line 31, and likewise receives the phase shifted signal by way of the circuit line 37. The wave form comparator 36 compares the gas sensor output and phase shifted signal with the reference output signal, and it measures the phase shift difference between the two signals inputted to it which provides, by means of the difference between the two signals, an indication of the delay required for the ultrasonic signal to pass between its transmittor 6 to its receiver 7, in proportion to its reference signal, and provides a signal difference that may be detected and calculated for furnishing an indication of data representative of the concentration of the gas passing through the gas sensor, and which, as previously explained, was detected therein by means of the ultrasonic wave transmission. This wave form comparator includes a component No. MC 14093, obtained from Motorola Corporation. This signal or output differential is conducted along the circuit line 38 to a duty cycle filter 39, which wave form is subject to filtering and conversion into a DC voltage, which is a direct indication of the time-to-fly, or influence of the concentration of gas within the gas sensor, upon the passage of the ultrasonic signal from its transmitter to its receiver. This DC voltage is inputted through the circuit line 40 and to a temperature compensation component, as at 41, so that the temperature previously determined by means of the temperature sensing means 21 can be corrected for the effects of temperature variation within the sample chamber 14, with respect to the gas or gaseous mixture that was sampled therein. This component 41 is available from Motorola Corporation as part No. LM 324. In addition, the temperature conpensated signal is conducted by way of the circuit line 42 to a signal conditioner 43, where optional pressure compensation, and/or humidity compensation, as by means of the component 43, may be made, if these two environments are of such magnitude that they have any influence upon the gas being detected within the gas sensor 1, and which requires adjustment in the representative signal so as to filter out the effects of these elements for attainment of a true signal representative of the concentration of the gas passing through the gas sensor, and being measured. This signal conditioner also incorporates components available from Motorola Corporation, under part No. LM324. In effect, the signal conditioner provides an offsetting function and a correction for span representative of the voltage differentials determined as a result of temperature compensation, pressure compensation, and humidity compensation, so that any deficiencies present in the representative signal as a result of these variations can be eliminated, to provide an output signal along the circuit line 44 that is representative of the converted signal that is true and accurate of the influence of the gas sample upon the passage of the ultrasonic waves within the gas sensor, and which may be readily calculated into a determination of the percentage of concentration of that gas within the tested sample. For example, there is readily available upon the market volt meters that are pregauged to provide a 0 volt output reading representative of a 0% of a particular gas within a flow line, such as oxygen, and nitrogen, in addition to a reading of 100% measurement of oxygen within the gas sample, upon detecting a reading of one volt output from the circuit line 44, after said output has been compensated for by means of the signal conditioner, as aforesaid. Obviously, this output signal could be transmitted, processed, and utilized for a variety of purposes, such as being passed through a modem for transmission over the telephone for conveyance of data to a remote location, for analysis, such as at the hospital, doctor's office, or the like, or the data could be transmitted to a remote nursing station, to provide an immediate readout and notification through an alarm in the event that the percentage of oxygen being generated within a concentrator may fall below an acceptable medical level, or for other related readings, as can be readily understood.

The same signal emanating from the signal conditioner may be transmitted by way of the circuit line 45 to an adjustable set point means 46, which may provide an indication, as through the previously explained type of alarm or other system that readily indicates when the operations of, for example, an oxygen concentrator may fall below acceptable levels of generation of oxygen as for use by the patient, or for other medical purposes. For example, an adjustable set point may be regulated to provide a warning when the oxygen being generated by an oxygen concentrator falls below an 85% desirable therapeutic usage level, and to alert any nurse, or nurse's aide, that something is malfunctioning in the operations of the concentrator as employed by a patient, or the hospital Another external input may be connected through the circuit line 47 so as to provide for an interrelationship between various systems as used in the hospital, and to provide an overide system where such may be desired. This may include a component No. MC 140920 from Motorola Corporation, to achieve these results. For example, if this gas sensor means is located within an oxygen concentrator device, when such a concentrator device is initially turned on, it may take a matter of minutes before it reaches acceptable operating levels, and an external output, such as an alarm, may be provided as an inhibiting may be provided for an inhibiting function to prevent any signal or warning to be given during that warmup stage, for a select period of time. This adjustable setpoint output may include components in the category of part No. LM 324, No. LM 393, No. MC 14093, and No. MC 14001, from Motorola Corporation.

Figure 8A:
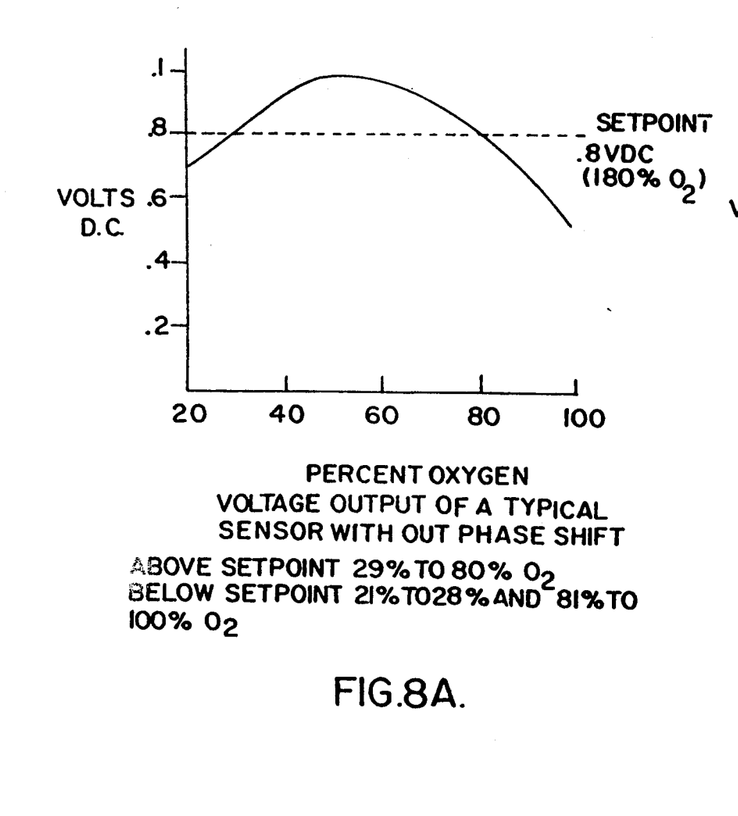
FIG. 8A is a graph disclosing a comparison of the volts versus the percentage of oxygen detected for a typical prior art ultrasonic gas measuring device.
Figure 8B:
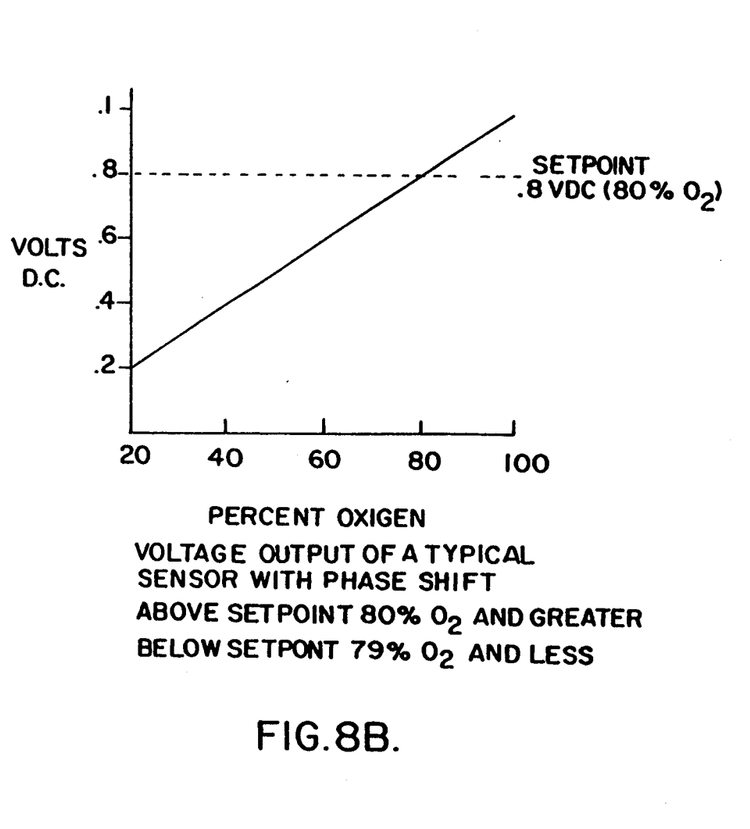
FIG. 8B shows a graph of the volts versus the percent of oxygen detected for the ultrasonic gas measuring device of this current invention.

The phase shift means 35 as previously referred to, is an integral part of the electronic circuitry that allows for the gas sensor assemblage to attain repeatability when they are manufactured in volume. Because the gas sensor assembly is subject to manufacturing tolerances, it is necessary to employ the use of the phase shift 35 to provide the proper phase relationship between the reference output of the oscillator and driver circuitry 30 and the output of the receive amplifier 33. An example of the effective application of phase shift within the circuitry to provide more accuracy and consistency in gas sensor output can be readily determined by viewing FIGS. 8A and 8B. For example, FIG. 8B discloses a graph of a gas sensor of this invention that incorporates phase shifting within its circuitry, and as can be seen, since the wave form outputs from the receive amplifier are shifted into alignment with the wave form output of the reference output wave form, there is always a consistent and linear readout of the relationship between the volts D.C. generated after signal conditioning, but which has been subjected to the wave form comparator that compared the two wave forms therein, after their signal phases have been adjusted into proper phase relationship, so that representative information by way of the detected volts D.C. can be readily converted into a representation of percentage of oxygen , as in the case of an oxygen concentrator, to give an accurate readout of between 20% to 100% of oxygen concentration within a generated gas. These types of readings can be consistently attained from all gas sensors that may be fabricated in volume, where their phase shift is properly set and provides for signal alignment, between the generated signal, through the gas sensor, and its reference signal, for all installations. On the other hand, as can be seen in FIG. 8A, utilization of the same gas sensor, either of the prior art, or of this current invention, where phase shifting of the gas detected representative signal is not made, as by means of a phase shift 35, when compared to a reference signal output, the shifting of the gas detected generated signal distorts, under certain conditions, so substantially that overlapping of the signals occur, which causes an aberration in the signal comparison, in the wave form comparator, such that when overlapping or a shifting out of phase of the signal in any amount between 0% to 360% in phase causes an inconsistency in the comparison of the wave forms, within the component 36, such that the volts D.C. detected under select conditions, may be misrepresentative of the actual percentage of oxygen generated within or by an oxygen concentrator. Thus, phase shifting provides the ability to utilize a larger amount of the reference wave form that is available when comparing with the wave form generated by the gas sensor, such that far more accuracy can be maintained and achieved as a result of such higher resolution when providing an indication as to the percentage of oxygen being generated within a concentrator, than can be attained from circuitry wherein phase shifting is ignored.

Figure 6:
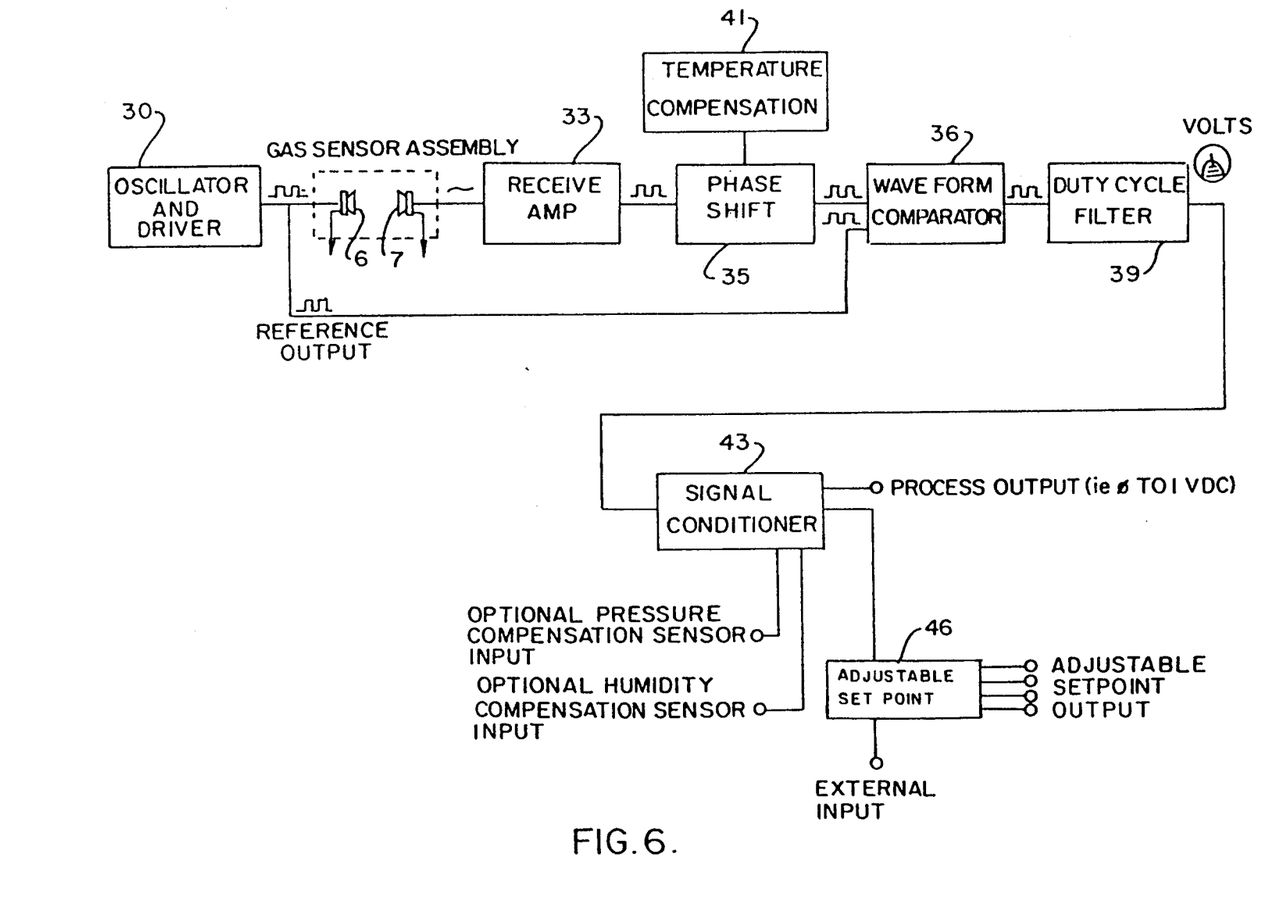
FIG. 6 is a block diagram of a modified structure and circuitry for the gas measuring device of this invention.

A modification to the block diagram of this invention can be seen in FIG. 6. Generally, all of the components reviewed, as shown, and their method of operation are similar if not identical to that which has already been described with respect to FIG. 5. The only difference is temperature compensation, as through a temperature compensator 41, that is located directly to coordinate with the phase shift 35, so that temperature compensation due to variations of the temperature of the gas samples being measured, may be made and compensated for during the phase shifting function, of the circuitry, so that adjustment for temperature can be made in an early stage of wave form analysis, and before the wave form comparator makes its comparison, and thereby effectively, as has been found, significantly enhances the operating temperature range for the gas indicator device As previously reviewed with respect to the analysis of the circuitry of FIG. 5, the temperature compensation method explained and shown therein utilizes the voltage created as an output of the duty cycle filter 39 to compensate for changes in temperature on the voltage level before being input into the signal conditioner 43. On the other hand, in this modification, the temperature compensation-phase shift relationship, when their functioning are interconnected, as shown in FIG. 6, makes use of the phase shift type circuitry to vary the phase of the received square wave, from the gas sensor, as a result of temperature changes, before any wave form comparing takes place. The proper relationship of the received wave form is still adjusted in accordance with the phase shift method, as previously described, however, the temperature sensor input changes that detected phase of the received wave form to maintain its proper phase relationship over a span of temperatures with a specific gas sample. In other words, the temperature effects on the passage of the ultrasonic waves through a gas specimen, between its transmitter 6 and receiver 7, are adjusted prior to any input of a signal into the wave form comparator 36, so that when wave form comparison is made, between the generate signal, and the reference output signal, temperature compensation will already have been remedied. This method of phase-shift temperature compensation may be accomplished with analog electronic circuitry, however, usage of the type of temperature compensation means 41, as previously explained, in cooperation with the type of phase shift 35, as previously reviewed, are generally integrated together to achieve this precompensation function, before delivery of its square wave output to the wave form comparator 36. Obviously, usage of the type of electronic structure as reviewed in this FIG. 6 is very useful when the gas measuring device of this invention is exposed, during usage, to gases that exhibit a wide range of temperature extremes, as in the case of its usage in combination with portable type analytical equipment.

Figure 7:
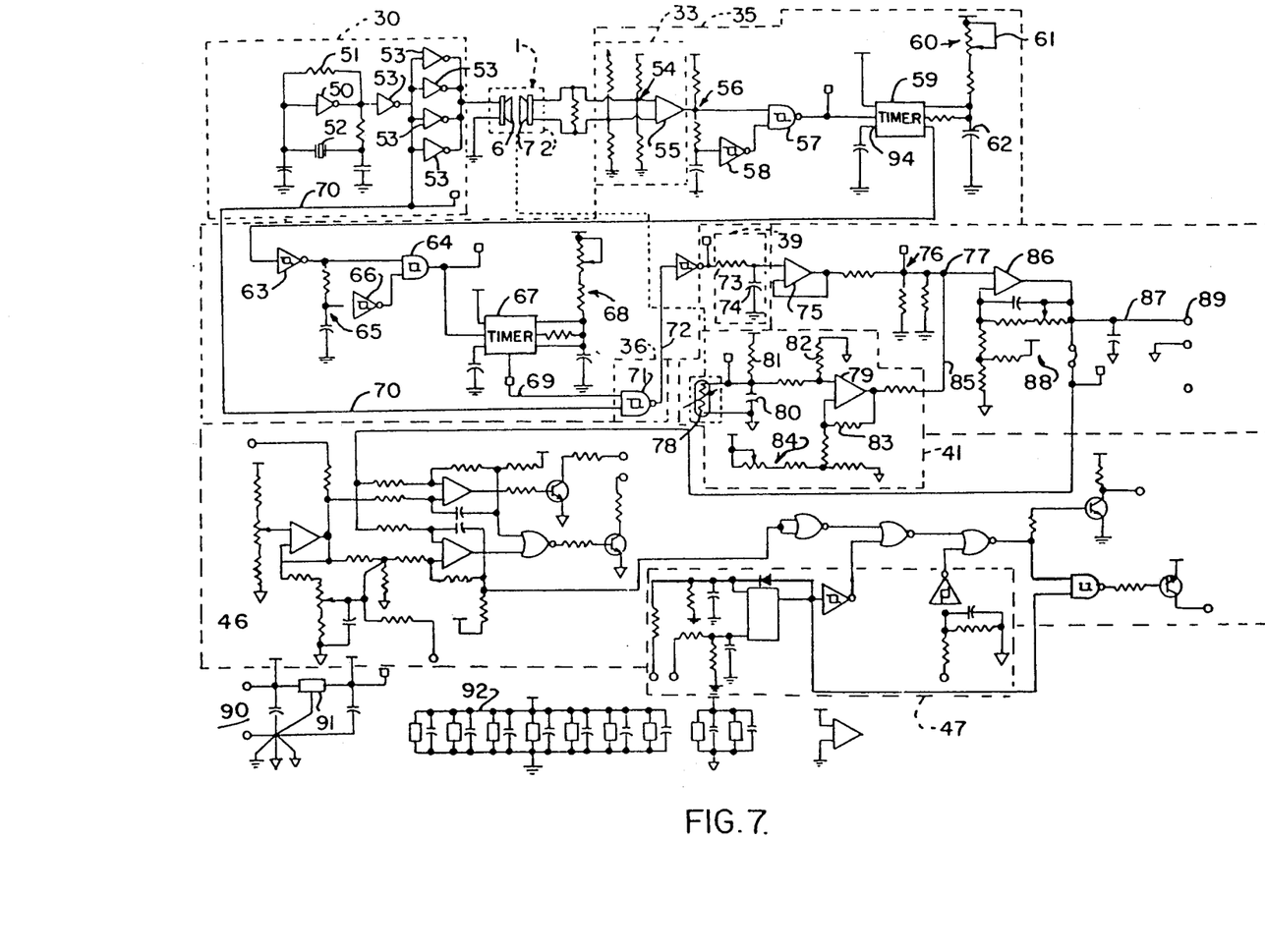
FIG. 7 is an electrical circuitry diagram expanding upon the block diagram shown in FIG. 5 of the drawings.

The more specific circuit diagram showing the various components embodied in this gas sensor assembly, and its electronic components, is shown as detailed in FIG. 7. In addition, the relationship of the components as disclosed in this figure are likewise outlined, as shown in phantom line, in order to depict the specific components as previously reviewed in FIG. 5, pertaining to the schematic block diagram of the circuitry of this invention. More specifically, the oscillator and driver component 30 includes an integrated circuit 50 that functions with the resistance 51 to achieve oscillation through the crystal resonator 52, for delivery of its signal through the integral gates 53 for providing additional drive current to the generated oscillating signal. These gates may be obtained from Motorola Corporation, as part No. MC 14049, as aforesaid. This signal is then delivered to the gas sensor assembly 1, and more specifically to its transmitter 6, for transmission across the chamber of the housing means 2 of the assembly, for reception by the receiver 7, in the manner as previously explained. This delayed signal, delayed due to the presence and existence of a gas within the chamber 2, which has a tendency to delay the transmission of any ultrasonic waves through the assembly, is then conducted to the receive amp 33 in the manner as previously explained, being part No. LM 393. Within the receive amp 33 the signal is subjected to a series of resistances, as at 54, wherein the signal is prepared for conversion by means of the integrated circuitry 55, as previously explained, being part No. LM 393, wherein the resistance is turned by the integrated circuit 55 on or off at the midpoint of the received sine wave, as received from the gas sensor, and therein converts its to a square wave having at least a 5 volt amplitude, or greater, depending upon its supply voltage, to be delivered to the phase shift 35. Within the phase shift, the amplified square wave signal is converted by the series resistance and capacitance, as at 56, into a trigger pulse, which is then delivered to the integrated circuitry 57, as previously explained, being part No. MC 14093, wherein said circuitry 57 and its gate 58, being part of the trigger pulse conversion circuitry, delivers the signal into a timer 59 (part No. ICM 7556), wherein the signal is then conducted to a delay circuitry 60 comprising the potentiometer 61 and the capacitor 62, for the purpose of delaying the leading edge of the pulse signal in preparation for its delivery to the wave form comparator 36 wherein it will be compared with the reference output, as will be described. The delayed signal is then delivered through another gate 63 (part No. MC 14584) of the identified integrator circuitry, wherein it is delivered to additional integrated circuitry 64 (part No. MC 14093) and its associated resistive capacitive network 65, and gated, as at 66 (part No. MC 14584), for delivery to the timer 67 (part No. ICM 7556) where the signal is once again delivered to a resistive capacitive network 68 for recreating the square wave signal at the adjusted delay level achieved through the functioning of the phase shift for its conducting by means of the circuit line 69 to the wave form comparator 36, as previously described, being part No. MC 14093. At the same time, the original reference signal, which is in the square wave form, is delivered by way of the circuit line 70 from the oscillator and driver circuitry 30 to said wave form comparator 36, wherein the delayed signal, as generated through its passage by means of the ultrasonic generator within the gas sensor assembly, is compared to the original reference signal, by means of this wave form comparator. The wave form comparator includes its integrated circuit 71, as previously reviewed, with its output being conducted over the circuit line 72 which is duty cycle dependent upon the two inputs from the circuit lines 69 and 70, which provides for the duty cycle comparative relationship between the two wave forms, for conduct of its difference over the circuit line 72 to the duty cycle filter 39. It is here processed by part No. MC 14584. The duty cycle filter also includes the combination of a resistance 73 and a capacitor 74 which outputs a D.C. voltage to the voltage follower 75 (part No. LM 324) of the signal conditioner. Since the duty cycle filter has eliminated the wave form to ground, by way of its capacitor 74, its output to the voltage follower 75 is a simple voltage reading, which is then filtered by means of the resistance and capacitor 76, for provision of a voltage reading at circuit point 77.

As previously explained, the temperature compensation 41 is useful for providing for an elimination of the effects of any temperature variation of the gas being measured within the gas sensor assembly, so that an empirical signal is being processed, and not one that is effected by any variations in temperature of the gas being measured. As can be seen in the temperature compensation 41, the temperature sensor 78 provides for the readout of a voltage based upon the temperature of the gas, and delivers said voltage reading to an operational amplifier 79 (part No. LM 324). The filter capacitance 80 provides an elimination of any noise interference, as generated within the gas sensor assembly, from the voltage reading, and the resistance 81 provides for maintaining a consistancy in the current flow through the temperature sensor, so as to assure the proper voltage input and regardless of the temperature being gauged. The resistances 82 and 83 provide for the amount of temperature gain correction established by the gas sensor assembly, while the gas is being measured. Thus, it provides for delivery of a voltage which is subjected to the multiplier effect of said resistances 82 and 83, depending upon the temperature measured, and the off-set value of its output signal. The offset low or 0 end of the range of voltages, normally maintained at 0 volts, is maintained by the offset circuitry 84, so that the voltage across the circuit line 85 is representative of the variations in temperature of the gas being measured, and that particular voltage is summed at the circuit point 77, to either add or subtract from that measured voltage from the duty cycle filter, and to eliminate the influence of temperature variation upon the measured voltage. The voltage at circuit point 77 is then conducted to the operational amplifier 86 (part No. LM 324), with the signal amplified therein being a true and accurate voltage representative of the ultrasonic wave delay as it passes through the gas within the gas sensor assembly. Thus, this provides a true reading of the effects of the gas upon the wave form, and which when compared with the span of the voltage representation which furnishes the range indicative of the percentage of concentration of the gas being measured, provides a readout voltage at circuit line 87 that could be further processed by external devices for providing some indication as to the concentration of the gas being tested. The span or range within which the computed voltage is measured is provided by the circuitry 88 that provides the amount of gain in voltage as desired for the upper limit of the voltage measurement span against which the voltage output at 86 is compared for determining a percentage of concentration of the gas being measured. Circuit point 89 relates to the process outputs as previously reviewed in the block diagram of FIG. 5.

The power supply is indicated at 90 and includes an input voltage of anything above 9 volts, and in this particular instance, comprises approximately 24.6 volts D.C. This voltage is then regulated to 5 volts, by means of the voltage regulator 91, and this particular voltage is then provided to all of the various integrated circuitry, as shown at 92, these being the various integrated circuits as previously described within the various components of the block diagram, and as reviewed within this circuit diagram. The power supplies are available from Motorola Corporation.

The adjustment set point outputs 46, as previously explained, provides circuitry for establishing set points with respect to the output voltage along circuit line 87, so that various indicators, alarms, or the like, can be initiated if the particular set points are achieved, relative to time, depending upon the parameters established for these controlling devices.

The external input 47 as previously explained can provide various additional controls, from external means, the set point outputs, such as, for example, a time delay means 93 (part No. MC 14020), that may be used for delaying the functioning of the set point outputs, and the adjustment means 46, until such time as the gas sensor assembly warms up to its proper and functional operating range. This has been previously explained.

It might be stated that the optional pressure compensation sensor input, as previously reviewed in the block diagram, or the optional humidity compensation sensor input, as likewise previously reviewed, which provides for compensation in the signal generated and the voltage derived as a result of the influence of the gas upon the ultrasonic wave form within the gas sensor assembly, will have their outputs likewise delivered to the signal conditioner, at the circuit point 77, so as to vary the voltage provided thereat, representative of the wave form differential through comparison of the reference output to the phase shifted output from the gas sensor assembly, so as to eliminate the influence of pressure and humidity, upon the output signal, similar to that which has been done, as explained herein at 41, for the temperature compensation. The pressure sensor is available from Sensym, Inc., and the humidity sensor is available from General Eastern Company.

Where the temperature compensation 41 is used in cooperation with the phase shift 35, as previously reviewed in the block diagram of FIG. 6, the temperature compensation output, as along circuit line 85, instead of varying the established voltage at circuit point 77, will be fed into the control voltage point 94 of the timer 59, and therein vary the amount of phase shift in relation to temperature so as to eliminate or compensate for temperature variation in any gas being measured.

Variations or modifications to the subject matter of this invention as described herein may occur to those skilled in the art upon reviewing the description of the invention as set forth. Such variations or modifications, if within the spirit of this invention, are intended to be encompassed within the scope of any claims to patent protection issuing upon this development. The description of the preferred embodiment set forth in this application is provided for illustrative purposes only.

Having thus described the invention, what is claimed and desired to be secured by Letters Patent is:

1. An ultrasonic gas measuring device for continuously monitoring the gas including a housing means, said housing means having a gas inlet and a gas outlet provided therethrough for passage of a gas to be measured, ultrasonic means provided within the housing means, said ultrasonic means having a transmitter and a receiver disposed at spaced locations at opposite positions of the housing means for transmission of its ultrasonic waves along the length of the passing gas, electronic means operatively associated with the housing means to measure the concentration of gas flowing therethrough, said electronic means including a receive amplifier which functions to detect and generate in cooperation with the ultrasonic means a signal corresponding to a concentration of a gas passing through and along the length of the housing means, said electronic means also including an oscillator and driver and generating a reference signal corresponding to the electronic signal delivered to the ultrasonic means, and electronic phase shift means electrically connected with the receive amplifier and effecting a shift of the first said generated signal to furnish a phased relationship between the generated signal and the reference signal, and signal conditioner means providing for revision of the generated signal due to one of temperature, pressure, and humidity compensation, wherein a larger span for comparison between the reference signal and the signal corresponding to the concentration of the gas provides greater accuracy in the measurement of the percentage of concentration of the passing gas.

2. The invention of claim 1 and wherein a pair of opposite end walls provided within the housing means, one of said transmitter and receiver of the ultrasonic means mounted upon one of each end wall, one of said walls being adjustable within the housing means to provide for a presetting in the functioning of the measuring device in determining the concentration of any gas passing through the housing means during its operation.

3. The invention of claim 2 wherein the adjustment of one of the end walls provided for phase shifting with respect to the gas concentration signal and the reference signal to provide for a wider range of comparison in the phased relationship between the two said signals when detecting and determining the concentration of the gas within the measuring device.

4. An ultrasonic gas measuring device for continuously monitoring a gas including a housing means, said housing means having a gas inlet and gas outlet provided therethrough for passage of a gas to be measured, ultrasonic means provided within the housing means, said ultrasonic means having a transmitter and a receiver disposed at spaced locations within the housing means for transmission of its ultrasonic waves through the passing gas, electronic means operatively associated with the housing means to measure the concentration of gas flowing therethrough, said electronic means functioning to detect and generate in cooperation with the ultrasonic means a signal corresponding to a concentration of a gas passing through the housing means, said electronic means also generating a reference signal corresponding to the electronic signal delivered to the ultrasonic means, and phase shift means provided within the electronic means and effecting a shift of the first said generated signal to furnish a wider span of comparison between the phase relationship between the generated signal and the reference signal wherein the concentration of a gas within a concentration range of that gas can be accurately determined.

5. The invention of claim 4 and wherein said electronic means providing for sensing temperature variations within the flowing gas and deflecting the phase shift means to provide for compensation in the signals generated and providing for a measurement of the concentration of the gas passing through the measuring device.

6. The invention of claim 4 and including means for producing an output signal representative of the percentage of concentration of gas being measured by the ultrasonic gas measuring device for detecting at least one percentage of concentration of the gas passing through the measuring device.

7. The invention of claim 6 and including means responsive to and indicating when a particular percentage of gas is being measured by the ultrasonic gas measuring device.

8. The invention of claim 7 wherein said indication means comprising an alarm means.

9. The invention of claim 4 and wherein said phase shift means is an electronic phase shift means.

10. The invention of claim 4 and wherein said housing means having a pair of opposite end walls, one of said transmitter and receiver of the ultrasonic means mounted upon one of such end wall, one of said end walls being adjustable within the housing means to provide for a presetting in the functioning of the measuring device for determining the concentration of any gas passing through the housing means during its operation.

* * * * *